(12) United States Patent
Botzem et al.

(10) Patent No.: US 6,348,593 B1
(45) Date of Patent: Feb. 19, 2002

(54) PROCESS FOR PREPARING FOLIC ACID

(75) Inventors: Jörg Botzem, Limburgerhof; Hagen Jaedicke, Ludwigshafen; Michael John, Lambsheim; Joachim Paust, Neuhofen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/497,151

(22) Filed: Feb. 3, 2000

(30) Foreign Application Priority Data

Feb. 25, 1999 (DE) .......................... 199 04 812

(51) Int. Cl.$^7$ .......................... C07D 475/00
(52) U.S. Cl. ............ 544/261; 562/440; 562/455; 568/414; 560/263
(58) Field of Search ............ 544/261, 248, 544/257; 562/490, 445; 568/414

(56) References Cited

U.S. PATENT DOCUMENTS

| 2,436,073 A | 2/1948 | Mowat et al. .............. 260/251 |
| 2,956,057 A | * 10/1960 | Kawanishi et al. |
| 4,080,325 A | * 3/1978 | Ellard |
| 5,159,117 A | 10/1992 | Wegner et al. .............. 568/312 |
| 5,410,056 A | 4/1995 | Wehrli ........................ 544/261 |

FOREIGN PATENT DOCUMENTS

| DE | 1254138 | * 11/1964 |
| EP | 122479 | 10/1984 |
| EP | 451835 | 10/1991 |
| EP | 472118 | 2/1992 |
| EP | 0 608 693 A2 | 8/1994 |
| WO | 99/20626 | 4/1999 |

OTHER PUBLICATIONS

Angier et al. "Synthesis of Pteroyglutamic Acid" JACS vol. 70 (1948).
Gangjee et al Journal of Heterocyclic Chemistry 1995, 32, pp. 243–247.*
Hawthorne et al Journal of Organic Chemistry 1963, 28(10), pp. 2831–2835.*

* cited by examiner

*Primary Examiner*—Gary Geist
*Assistant Examiner*—Paul A. Zucker
(74) *Attorney, Agent, or Firm*—Keil & Weinkauf

(57) ABSTRACT

A process for preparing folic acid, which comprises reacting a tetraalkoxypropanol of the general formula I,

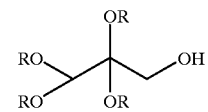

in which the substituents R are $C_1$–$C_4$-alkyl, with triaminopyrimidone of the formula II and p-aminobenzoyl-L-glutamic acid of the formula III

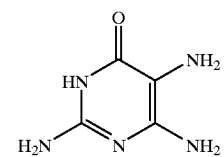

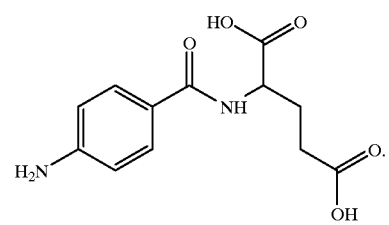

11 Claims, No Drawings

PROCESS FOR PREPARING FOLIC ACID

The present invention relates to a novel process for preparing folic acid.

Robert B. Angier et al. (JACS, 70 (1948), 25) describe the preparation of folic acid using halogen-free compounds by reacting diethyl p-aminobenzoyl-L-glutamate with 2-hydroxymalonaldehyde, isolating diethyl p-(2,3-dihydroxypropenylideneamino)benzoylglutamate, and reacting the intermediate with triaminopyrimidone.

Other preparation methods are described in: O. Isler, G. Brubacher, S. Ghisla, B. Kräutler, Vitamine II; G. Thieme Verlag Stuttgart (1988).

A low yield of folic acid is common to all these methods.

In addition, EP-A-0 608 693 describes a process for preparing folic acid in which 2-substituted malonaldehydes are reacted with p-aminobenzoyl-L-glutamic acid to form the corresponding diamine, which is reacted with triaminopyrimidone in the presence of sulfite to give folic acid. The disadvantage of this process is the difficulty of obtaining 2-substituted malonaldehyde.

It is an object of the present invention to provide a process for preparing folic acid with which folic acid is obtained in good yields by use of easily obtainable starting materials.

We have found that this object is achieved by a process for preparing folic acid, which comprises reacting a tetraalkoxypropanol of the general formula I,

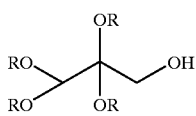
I in which the substituents R are $C_1$–$C_4$-alkyl, with triaminopyrimidone of the formula II and p-aminobenzoyl-L-glutamic acid of the formula III

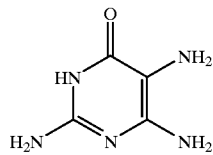
II

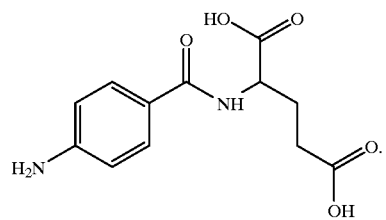
III

Alkyl radicals for R mean $C_1$–$C_4$-alkyl radicals, for example methyl, ethyl, n-propyl, isopropyl or n-butyl, preferably methyl or ethyl, particularly preferably methyl.

It has now been found, surprisingly, that folic acid can be obtained in high yields by using tetraalkoxypropanol of the formula I, in particular tetramethoxypropanol which is easily obtainable industrially by electrochemical oxidation of methylglyoxal dimethyl acetal.

For the purpose of the process according to the invention, it is possible in the first reaction step to react the tetraalkoxypropanol both with triaminopyrimidone of the formula II and with the p-aminobenzoyl-L-glutamic acid of the formula III, the reaction advantageously taking place under acid conditions at a pH below 4 and at a temperature in the range from 0 to 100° C.

The first reaction is preferably that of the tetraalkoxypropanol with the p-aminobenzoyl-L-glutamic acid of the formula III.

The reaction can take place in aqueous medium, where appropriate with the addition of inert, water-miscible, organic solvents such as acetonitrile, tetrahydrofuran, dimethylformamide, methanol, ethanol etc.

The acid reaction conditions can be adjusted, for example, by adding aqueous mineral acids such as aqueous hydrochloric acid, sulfuric acid, phosphoric acid, by adding organic $C_1$–$C_4$-carboxylic acids such as formic acid, acetic acid or propionic acid or by means of an acidic ion exchanger. Preferred acids in this connection are aqueous hydrochloric acid, formic acid and acetic acid.

Under the acidic hydrolysis conditions, the ketones of the general formula Ia

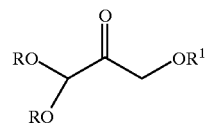
Ia in which the substituents R are $C_1$–$C_4$-alkyl, $R^1$ is hydrogen or —C(=O)—$R^2$ and $R^2$ is hydrogen or $C_1$–$C_3$-alkyl, can be prepared from the corresponding compounds of the general formula I.

Alkyl radicals for R mean the $C_1$–$C_4$-alkyl radicals already mentioned above.

Alkyl radicals for $R^2$ mean $C_1$–$C_3$-alkyl radicals such as methyl, ethyl, n-propyl or isopropyl.

Preferred radicals for $R^2$ are hydrogen or methyl.

Very particularly preferred ketones of the formula Ia are those in which R is methyl and $R^1$ is hydrogen or acetyl [—C(=O)—$CH_3$].

The reaction, which has been mentioned at the outset and is preferably carried out, of tetraalkoxypropanol with p-aminobenzoyl-L-glutamic acid of the formula III can, under the abovementioned acidic conditions, lead in situ via the ketones of the general formula Ia to the intermediates of the general formula IV,

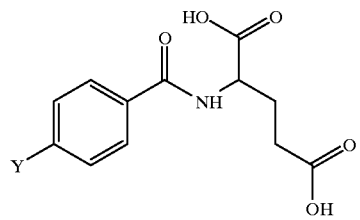
IV in which the substituent Y is

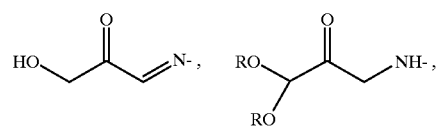

-continued

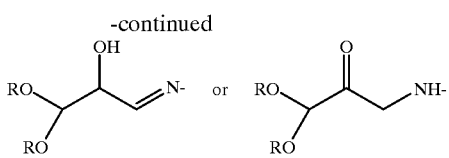

and R is $C_1$–$C_4$-alkyl, preferably methyl.

The reaction of compounds of the formula IV with triaminopyrimidone of the formula II advantageously takes place in the presence of sulfite, or inorganic compounds which form sulfites in water, at a pH of from 3 to 8 and temperatures of about 0 to 100° C.

The employed sulfites or inorganic compounds which form sulfites in water are compounds such as $Na_2SO_3$, $K_2SO_3$, $H_2SO_3$, $NaHSO_3$, $Na_2S_2O_5$ or $SO_2$ and the like. It is likewise possible to employ triaminopyrimidone sulfite.

The intermediates Ia and IV formed in the folic acid preparation according to the invention can be isolated after their preparation and then employed further in the process according to the invention. However, they can also be prepared in situ, and the reaction can accordingly also be carried out in a one-pot reaction.

The invention also relates to ketones of the general formula Ia

Ib

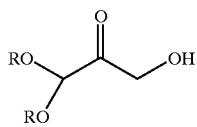

in which the substituent R is $C_1$–$C_4$-Alkyl.

Preferred ketones of the general formula Ib are those in which the substituent R is methyl.

The invention likewise relates to compounds of the general formula IV

IV

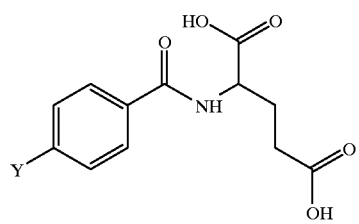

in which the substituent Y is

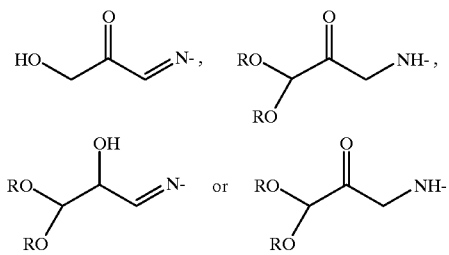

and R is $C_1$–$C_4$-alkyl, preferably methyl.

EXAMPLE 7.5 g of 2,2,3,3-tetramethoxy-1-propanol were dissolved in 25 ml of acetic acid and heated to reflux. About 1.5 g of a low boiler were distilled off. After a reaction time of two hours, distillation was carried out under 20 mbar. At 110 to 120° C., 5.8 g of a fraction of about 80% acetoxymethylglyoxal dimethyl acetal (A) and 12% hydroxymethylglyoxal dimethyl acetal (B) distilled.

A

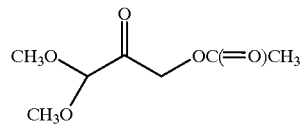

B

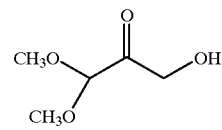

We claim:
1. A process for preparing folic acid, which comprises reacting a tetraalkoxypropanol of the general formula I,

I

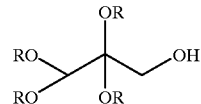

in which the substituents R are $C_1$–$C_4$-alkyl, with triaminopyrimidone of the formula II and p-aminobenzoyl-L-glutamic acid of the formula III

II

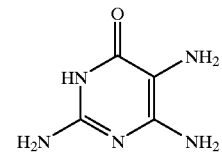

III

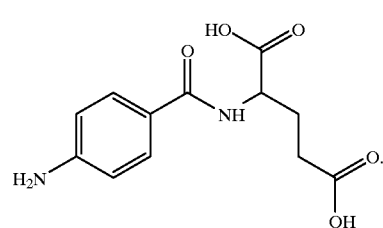

2. A process as claimed in claim 1, wherein firstly tetraalkoxypropanol of the general formula I is reacted with p-aminobenzoyl-L-glutamic acid of the formula III, and subsequently the product formed in the reaction is reacted with triaminopyrimidone of the formula II to give folic acid.

3. A process as claimed in claim 1, wherein firstly tetraalkoxypropanol of the general formula I is reacted with triaminopyrimidone of the formula II, and subsequently the product formed in the reaction is reacted with p-aminobenzoyl-L-glutamic acid of the formula III to give folic acid.

4. A process as claimed in claim 1, which is carried out as a one-pot reaction.

5. A process as claimed in claim 1, wherein the reaction with triaminopyrimidone takes place in the presence of sodium sulfite.

6. A process as claimed in claim 1, wherein the tetraalkoxypropanol of the general formula I is hydrolyzed with acid before the reaction with the compounds of the formulae II and/or III.

7. A process as claimed in claim 6, wherein the tetraalkoxypropanol of the general formula I is hydrolyzed before the reaction with the compounds of the formulae II and/or III in the presence of a $C_1$–$C_4$-carboxylic acid to give the ketone of the general formula Ia

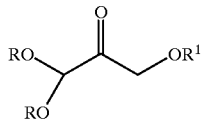

Ia in which the substituents R are $C_1$–$C_4$-alkyl, $R^1$ is hydrogen or —C(=O)—$R^2$ and $R^2$ is hydrogen or $C_1$–$C_3$-alkyl.

8. A process as claimed in claim 1, wherein tetramethoxypropanol is reacted with triaminopyrimidone of the formula II and p-aminobenzoyl-L-glutamic acid of the formula III.

9. A ketone of the general formula Ib

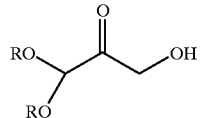

Ib in which the substituent R is $C_1$–$C_4$-alkyl.

10. A ketone of the general formula Ib as claimed in claim 9, in which the substituent R is methyl.

11. A compound of the formula IV

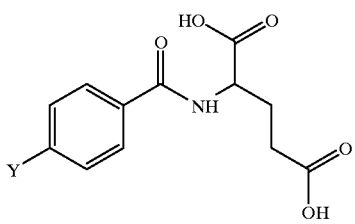

IV in which the substituent Y is

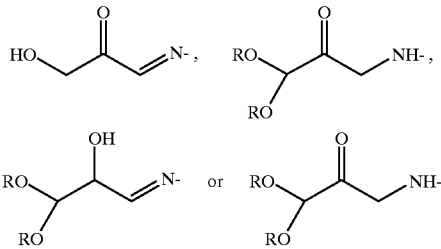

and R is $C_1$–$C_4$-alkyl.

* * * * *

UNITED STATES PATENT AND TRADEMARK OFFICE
CERTIFICATE OF CORRECTION

PATENT NO. : 6,348,593 B1
DATED : February 19, 2002
INVENTOR(S) : Botzem et al.

It is certified that error appears in the above-identified patent and that said Letters Patent is hereby corrected as shown below:

<u>Title page,</u>
Item [30], "Feb. 25, 1999" should be -- Feb. 5, 1999 --.

Signed and Sealed this

Eleventh Day of June, 2002

*Attest:*

*Attesting Officer*

JAMES E. ROGAN
*Director of the United States Patent and Trademark Office*